United States Patent [19]
Besnier

[11] Patent Number: 5,605,094
[45] Date of Patent: Feb. 25, 1997

[54] APPARATUS FOR THE DECONTAMINATION OF CONTAINERS CONTAINING RADIOACTIVE LIQUID

[75] Inventor: Joseph Besnier, Acqueville, France

[73] Assignee: Compagnie Generale des Matieres Nucleaires, Velizy-Villacoublay, France

[21] Appl. No.: 404,260

[22] Filed: Mar. 15, 1995

[30] Foreign Application Priority Data

Mar. 16, 1994 [FR] France .................................. 94 03055

[51] Int. Cl.$^6$ ................................ B30B 9/00; B08B 3/00
[52] U.S. Cl. ........................ 100/70 R; 100/92; 100/94; 100/102; 100/902; 134/59; 134/62; 134/115 R
[58] Field of Search ..................................... 100/70 R, 92, 100/94, 102, 902; 134/59, 62, 115 R

[56] References Cited

U.S. PATENT DOCUMENTS

| | | | |
|---|---|---|---|
| 4,324,264 | 4/1982 | Kröger et al. ............................. | 134/68 |
| 5,174,344 | 12/1992 | Gonzalez-Miller et al. ........... | 100/902 |
| 5,371,911 | 12/1994 | Mullinax ................................. | 100/902 |
| 5,456,167 | 10/1995 | George et al. ............................ | 134/62 |

FOREIGN PATENT DOCUMENTS

| | | |
|---|---|---|
| 3143078 | 5/1983 | Germany . |
| 3509839 | 9/1986 | Germany . |
| 3520411 | 1/1987 | Germany . |

Primary Examiner—Stephen F. Gerrity
Attorney, Agent, or Firm—Pearne, Gordon, McCoy & Granger

[57] ABSTRACT

A unit for the rapid and reliable decontamination of containers containing contaminated liquids. The apparatus automatically receives, opens, empties, rinses and dries the containers individually. The containers may be sorted as a function of their residual contamination. The containers may optionally be crushed at a temperature at which they are rendered fragile. The containers, whether uncrushed or crushed, are then put into storage or waste canisters. The soiled or contaminated liquids are received by separate collectors.

14 Claims, 11 Drawing Sheets

APPARATUS FOR THE DECONTAMINATION OF CONTAINERS CONTAINING RADIOACTIVE LIQUID

BACKGROUND OF THE INVENTION

The invention relates to a unit and a process for the decontamination of containers containing radioactive liquid.

A typical application of the invention would be in a radioactive liquid analysis installation, where radioactive samples are poured into containers. The containers have two parts, a sealing stopper and a jug. The containers are transferred through the pipes of a pneumatic transfer system from one shielded unit to another. The final destination of the containers is a unit in which their residual content is emptied, and the containers are decontaminated. Currently, containers are accumulated until a sufficiently large batch has been collected, after which, following emptying and possible crushing, they are put into a decontamination tank filled with washing liquid and are left there for several hours, after which they are recovered and stored. The current means of decontamination does not sufficiently decontaminate the containers and under existing standards the containers must be buried in bitumen, concrete or glass drums at a great depth in a specialized installation. The current process is expensive, occupies a considerable volume and may become impermissible if stricter reprocessing standards are adopted.

The ultimate aim of the invention is to improve the reprocessing characteristics of spent containers. This requires that decontamination take place rapidly following the filling of the container with the liquid to be sampled and analyzed, e.g. one hour afterwards, which is possible in numerous cases by rapidly performing the sampling operations and the measurements. It has in fact been found that the adsorption or incrustation of contaminating solutes of the liquid on the plastic wall of the container was not completed after this brief period, whereas it is irreversible after one or two days. This lengthy waiting time is typical of existing installations. The benefit of a rapid decontamination is a limited residual contamination of the containers, which makes it possible to store them, at a much lower cost and with fewer constraints, in surface facilities.

It has also been found that the crushing of polluted containers prior to decontamination increases the incrustation of contaminants. Therefore, the invention decontaminates the containers prior to crushing by carefully washing the containers, which is made possible without using a large quantity of washing liquid, e.g. less than 100 to 200 ml per container. Crushing takes place on decontaminated containers making it possible to reduce their volume in the drums or storage canisters without any prejudicial effect resulting therefrom.

SUMMARY OF THE INVENTION

The decontamination unit proposed here comprises, in its most general form, a container supply apparatus, a container opening apparatus, at least one container washing and drying apparatus and a container scrapping means.

Each container arriving at the unit is treated as rapidly as possible. If several containers arrive roughly at the same time, they are brought into a waiting line or queue, but in spite of this are treated relatively rapidly. Thus, the unit contains a means for controlling the decontamination by regulating the flow of containers at the unit entrance. This is accomplished by a turntable receptacle with container reception cavities. The container rinsing and drying means are comprised of a means responsible for the interior of the jugs, a means responsible for the exterior of the jugs and a means responsible for the interior of the container stoppers used for sealing the jugs.

The decontamination process consists of opening, emptying and then individually washing the containers in a decontamination unit. The containers are then dried. Next, the containers are crushed. It is also possible to sort them prior to crushing as a function of their residual radiation contamination.

BRIEF DESCRIPTION OF THE DRAWINGS

The invention is described in greater detail hereinafter in a non-limitative exemplified manner and with reference to the attached drawings, wherein show.

DETAILED DESCRIPTION OF THE PREFERRED EMBODIMENT

Figure 1:
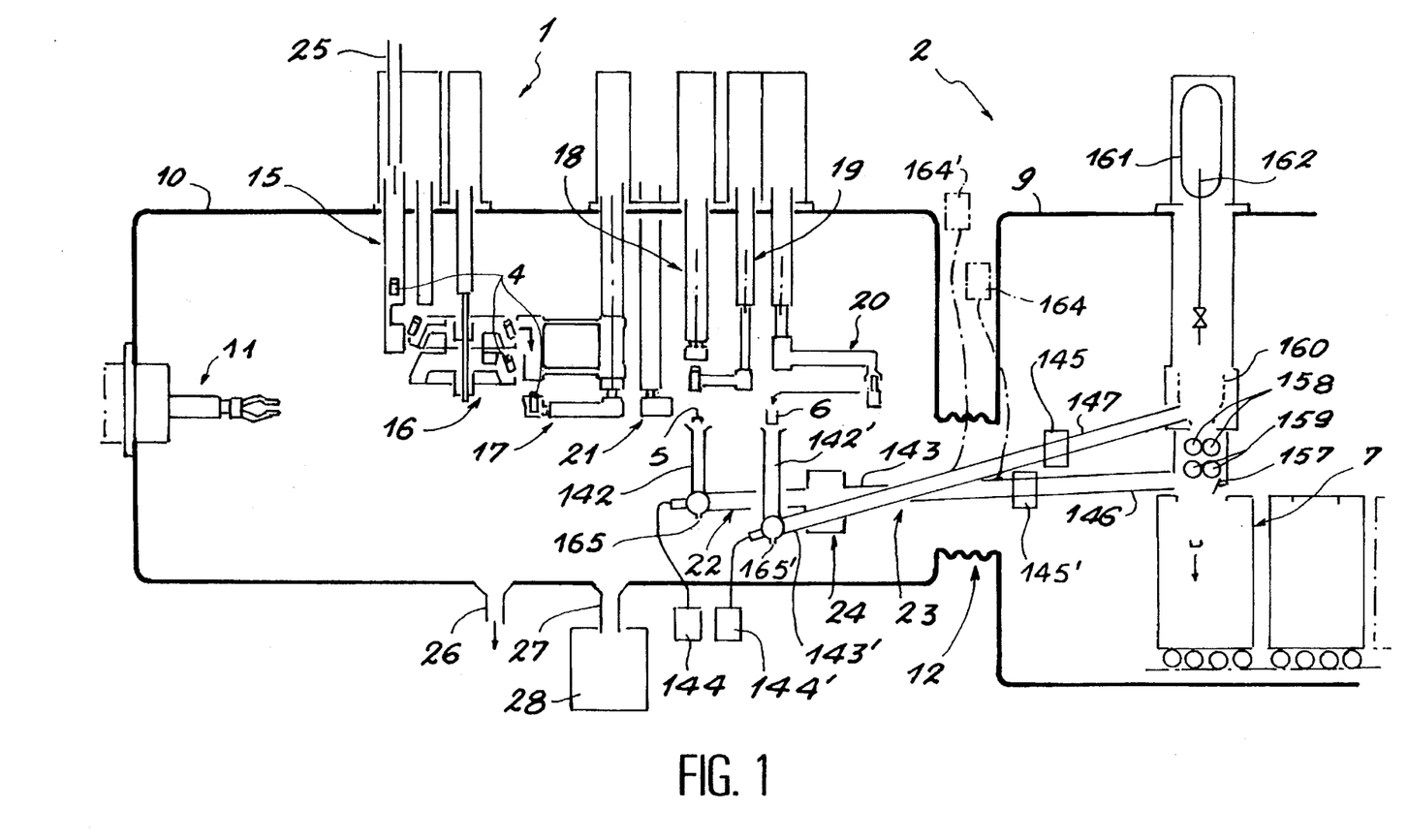
FIG. 1 An overall view of the unit.

Referring to FIG. 1, the decontamination unit is located in a first shielded enclosure 1, whose radiation protection wall is in the form of a first box or case 10 having recesses traversed by grippers or tongs 11 manipulated from the outside in order to permit handling operations and an outlet port surrounded by a bellows 12, which extends up to an entrance port of another shielded enclosure, or first scrapping enclosure 2 for the final stages of the treatment of the objects undergoing decontamination, namely the scrapping stages following the actual decontamination. The first scrapping enclosure 2 is defined by a second case or box 9, which is radiation-proof, but which can be thinner than the preceding case, because it only receives decontaminated containers.

The apparatus present in the first case 10 and serving for decontamination purposes are in the order of the stages of the process, an entrance chute 15, a waiting turntable 16, a gripping arm 17, an unscrewing device 18, a stopper washer 19, a first jug washer 20, a second jug washer 21, a stopper discharge system 22 and a jug discharge system 23. A radioactivity counter 24 is placed in front of portions of the discharge systems 22 and 23. The first case 10 also communicates with a container introduction pipe 25, a contaminated liquid recycling collector 26 and an effluent collector 27 terminated by a tank 28.

The washers 19, 20 and 21 comprise rotary arms for seeking the plugs or stoppers and also the jugs, for bringing them to particular locations and for setting them down. The waiting turntable 16 and the gripping arm 17 also rotate for the same reasons. Moreover, the unscrewing device 18 has parts rotating about an axis. The jugs and the stoppers consequently pass from one device to the other in the first case 10, without any manipulation by the grippers 11, which only serve for maintenance or emergency purposes. The devices of the first case 10 are controlled from the exterior, by a computer programmed to control motors used to maintain the line of all the containers entering into the first case 10 and for making them advance along the decontamination chain as rapidly as possible. The motors are located outside the first case 10 and are terminated by transmissions, which extend up to the mobile parts of the devices which they drive. The transmissions pass through sleeves, or preferably multiple joint spindles, ensuring a perfect seal between the interior and the exterior and which traverse the wall of the first case 10. Each of these means will be described in greater detail hereinafter. This arrangement makes it possible to locate all the sensitive equipment outside the first case 10, while leaving the components that are expected to never require repair inside the front case 10. It is clear that the manipulations by the grippers 11 are difficult and consequently inefficient for sensitive members such as sensors and actuators.

Momentarily leaving FIG. 1, a description will now be given of the devices of the first case 10. Some of these devices are well known and do not form part of the present invention, but merely contribute to the overall process. Consequently, they will not be described in detail.

Figure 2:
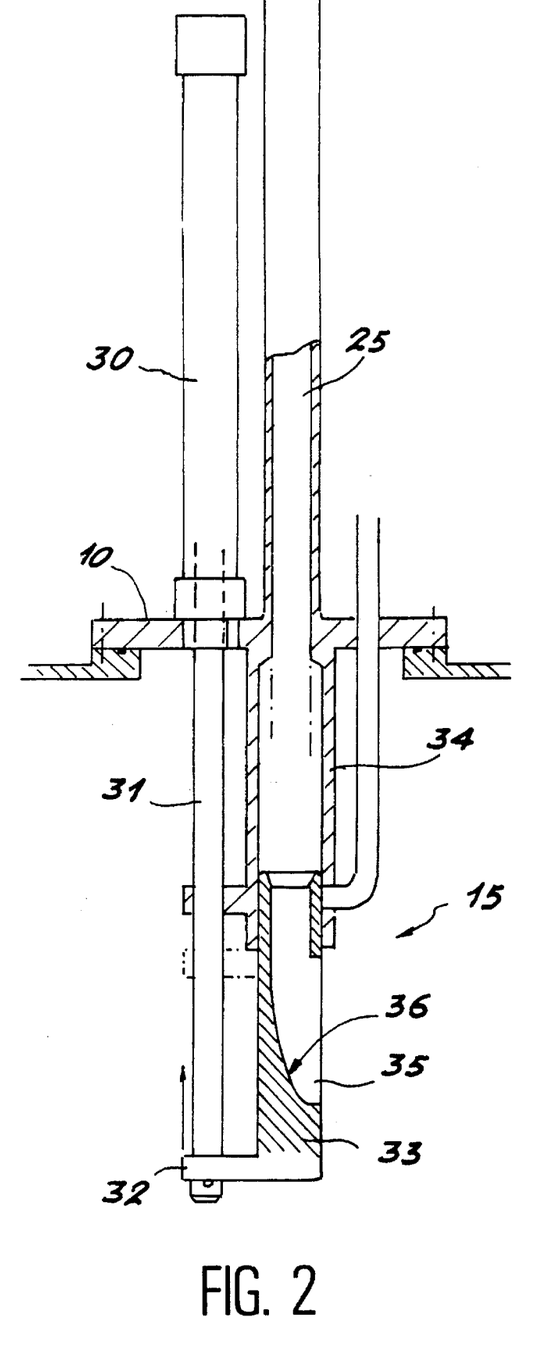
FIG. 2 A representation of a chute for introducing the containers into the decontamination unit.

The entry chute 15 is depicted in FIG. 2 and is located at the end of the introduction pipe 25, which belongs to a known pneumatic container transfer system. Its essential part is a mobile means moved by a jack 30 fixed to the outside of the first case 10 and which is traversed by the rod 31 of the jack 30. The rod 31 is terminated by a bracket 32 carrying a rod 33, which slides in accordance with the movements of the rod 31 in a sleeve 34 fixed to the introduction pipe 25 and which extends the same. The rod 33 is recessed and open by a lateral slit 35, which issues into the first case 10 in the position shown permitting the introduction of containers onto the lateral slit 35 of the containers into the first case 10, but which is masked by the sleeve 34 when the rod 33 is retracted. Retraction takes place as soon as a container has been introduced so that the polluting vapours of the first case 10 do not enter the pneumatic transfer system. It is pointed out that the ejection of the containers is facilitated by a rounding or streamlining 36 of the ring 33, which projects the containers towards the lateral slit 35.

Figure 3:
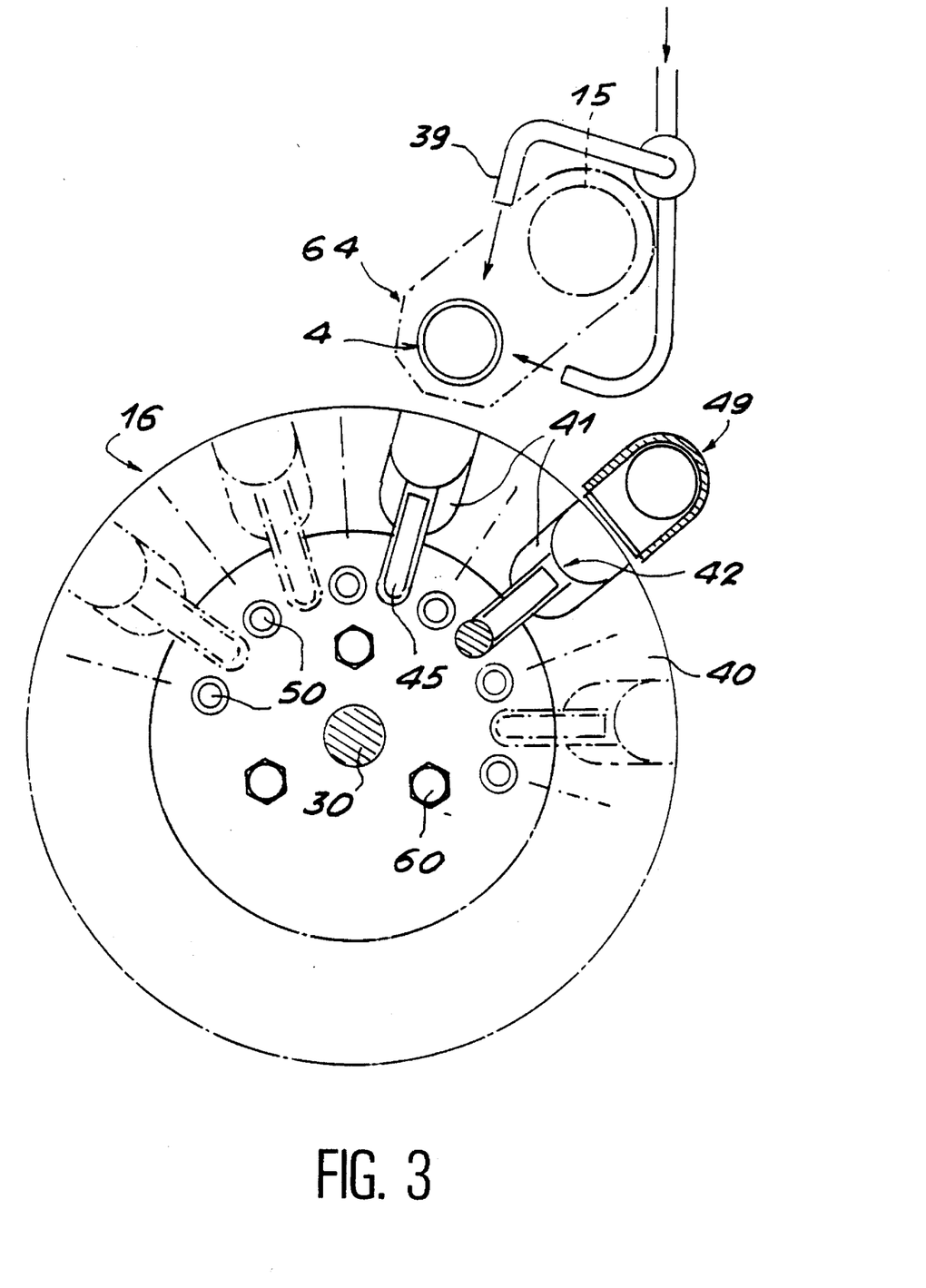
FIG. 3 Plan view of a turntable contiguous with the chute in order to regulate the flow of containers by creating a queue.
Figure 4:
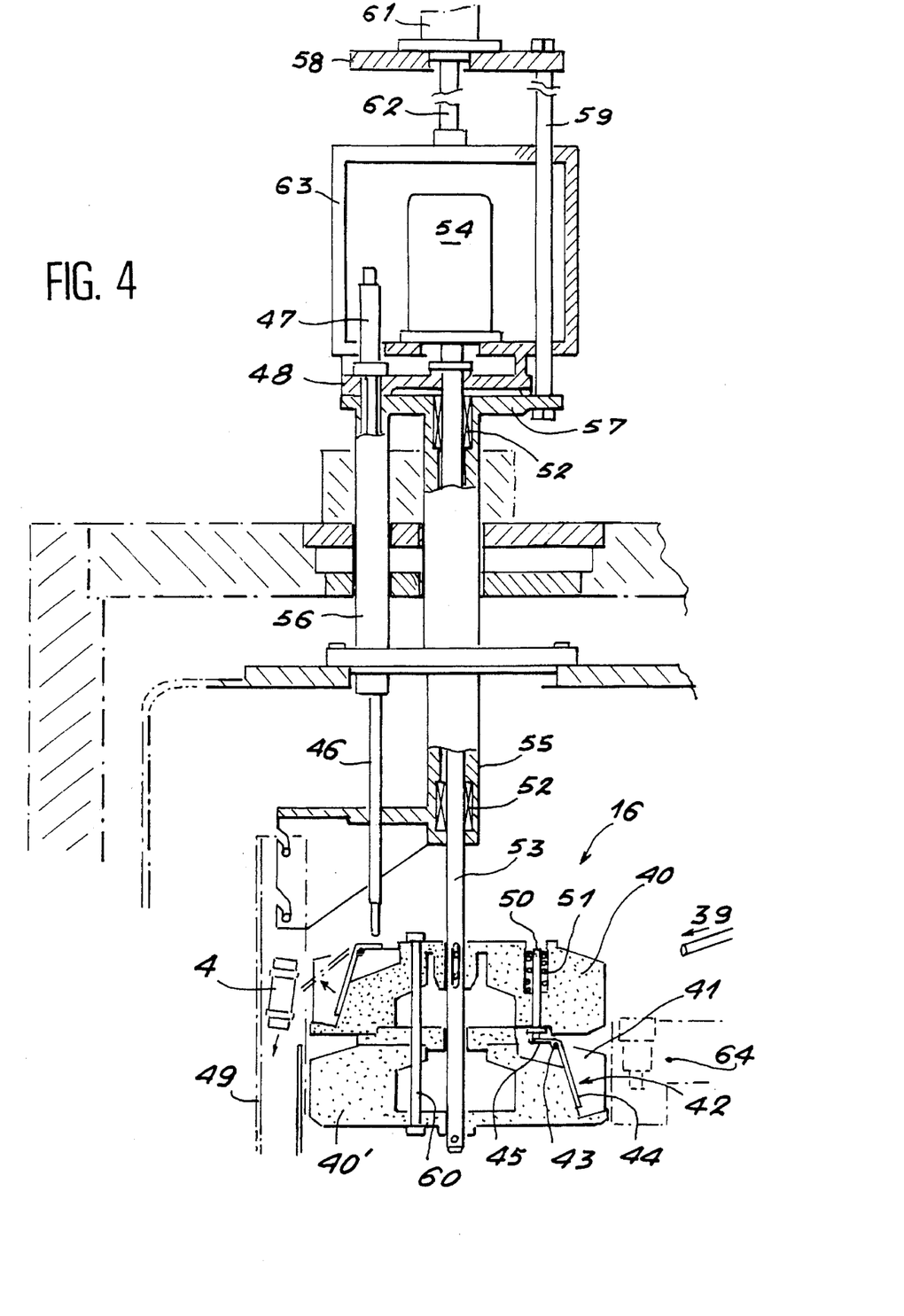
FIG. 4 Vertical sectional view of a turntable contiguous with the chute in order to regulate the flow of containers by creating a queue.

FIGS. 3 and 4 depict the waiting turntable 16 that receives the containers 4 after they leave the chute 15. This apparatus is identical to that described in greater detail in French patent application 93 10149. It is essentially formed by at least one rack, and preferably two racks 40, 40' joined by screws 60. The racks 40, 40' are superimposed and suspended on a shaft 53. Each of the racks 40, 40' is circular and has cavities 41 on its periphery. Each cavity being provided with a push rod 42 in the form of a bent lever articulated in its center 43, forming an ejector arm 44 and a control arm 45. The tilting of the push rods 42 is controlled by a single pin 46 constituting the rod of a jack 47, whose body is screwed to a platform 48 outside the first case 10. When the pin 46 is advanced, it pushes the end of the control arm 45 and thus projects the ejector arm 44 towards the outside of the cavity 41 in question in order to empty its content into a channel 49. When the pin 46 is released, the ejector arm 42 drops to the bottom of the cavity 41.

The superimposing of the racks 40, 40' makes it possible to store a larger number of objects, but leads to a few operational problems which are solved in the following way. Pistons 50 pass through the upper rack 40 where the pistons lower faces almost touch the control arms 45 of the push rods 42 respectively associated therewith of the lower rack 40' so that the pin 46, whose travel is immutable, strikes the push rods 42 of the upper rack 40 in a direct manner and those of the lower rack 40' by means of the pistons 50 in order to exercise the desired control. Springs 51 located in bores of the upper rack 40 in the inoperative state force the pistons 50 upwards in order to ensure that the push rods 42 of the lower rack 40' drop to the bottom of the cavities 41 when the pistons 50 are released.

The shaft 53 on which the racks 40 and 40' are suspended rotates under the action of a motor 54, which may or may not be associated with a mechanical coder, screwed to the platform 48. A jacket 55 is integral with the first case 10 and surrounds most of the length of the shaft 53 in order to protect and support it by means of a pair of plain bearings 52. Another jacket 56 arranged in the same way is located round the pin 46. The two jackets 55, 56 are joined by a base plate 57, which is itself connected to an upper plate 58 by vertical standards 59. The body of a jack 61 is screwed to the upper plate 58 and to its rod 62 is attached a pod or nacelle 63 integral with the platform 48. This arrangement makes it possible to raise and lower the platform 48, the jack 47 and the mobile turntable 16 by the Jack 61 in order to replace each of the racks 40, 40' level with the entry chute 15 and the orifice of the channel 49. The channel 9 is suspended on the jacket 55 and remains stationary in the first case 10.

On leaving the entry chute 15, the containers 4 drop onto a fixed balance 64. An empty cavity 41 of one of the two racks 40, 40', as a function of the state of the jack 61, is placed in front of the balance 64 and an air jet from nozzles 39 projects the container 4 into the cavity 41.

The interest of a mobile turntable 16 in this application is due to the fact that it is necessary to quickly decontaminate containers 4 which have become useless and arrive rapidly and at any time and because of the fact that the invention is used for individual decontamination of the containers 4. However, the decontamination unit has no control over the arrival of the containers 4. Therefore, it is necessary for the decontamination unit to regulate their flow. The turntable 16 serves as a waiting line or queue for containers 4, which it receives in cavities 41 and discharges in turn into the channel 49 as soon as the other equipment is freed. The automatic control program of the decontamination unit, which drives and coordinates all the equipments of the cases 1 and 2, is designed to retain the cavities carrying the containers arriving first. As decontamination takes place rapidly, the waiting times are greatly reduced, which does not compromise the quality of the end result.

Figure 5:
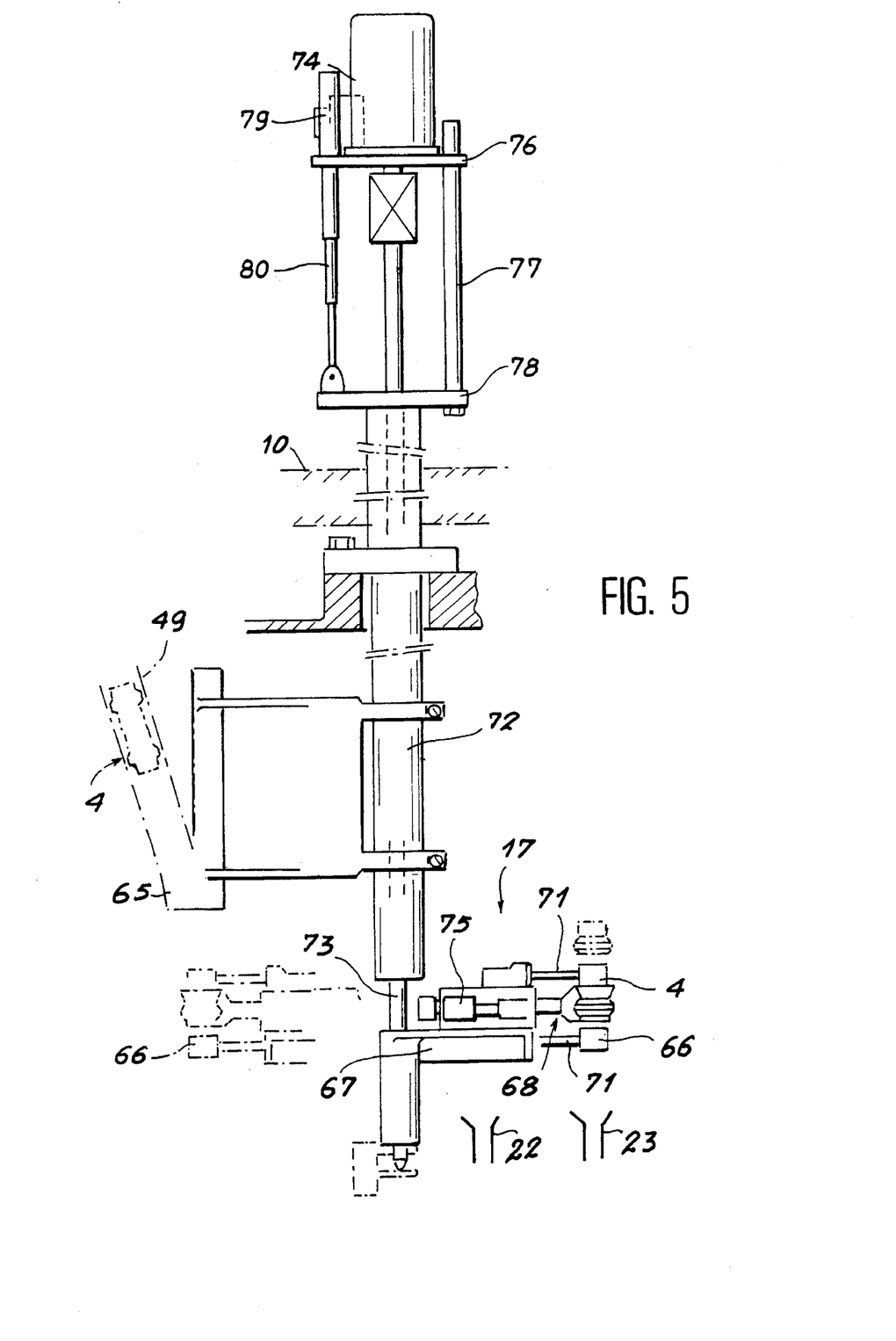
FIG. 5 Side view of a gripping arm.
Figure 6:
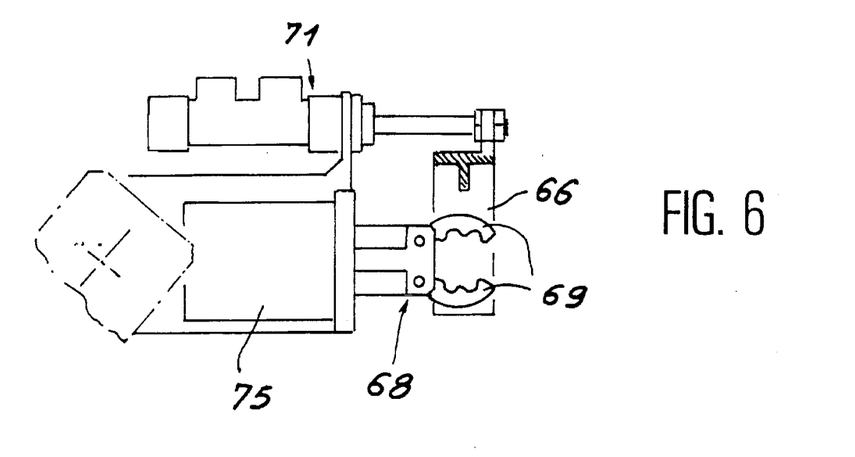
FIG. 6 Plan view of a gripping arm.

FIGS. 5 and 6 depict the gripping arm 17. Such an apparatus is already described, with an unscrewing device 18, shown in FIG. 7, and a liquid sampling means, in French patent application 93 12216 of the applicant and will consequently not be described in great detail here. On leaving the channel 49, the containers 4 drop into a guide pipe 65 and then onto a bottom 66 located at the end of a rotary section 67 of the gripping arm 17. A gripper 68 is fixed to the rotary section. The gripper 68 is equipped with jaws 69 which extend slightly above the bottom 66 and close around the container 4 which has just fallen through guide pipe 65. FIG. 5 shows the bottom 66 remote from the channel 49, because the gripping arm 17 has rotated. However, the gripping arm 17 is positioned under the guide pipe 65 as shown by the dashed lines when a container 4 is to be received as described above.

The bottom 66 is connected to the gripping arm 17 by rods of a jack 71 permitting the retraction thereof. If the gripper 68 then opens, the previously held container 4 is released and dropped. Release of the container 4 occurs above the entrance hopper 142 (FIG. 1) of the jug discharge system 23 so that the container 4 falls on to the entrance hopper 142. The container 4 is not released until the following operations are performed.

The guide pipe 65 is supported by a jacket 72 that extends through the first case 10. The jacket 72 houses a spindle 73 used for moving the rotary arm 67, by means of a motor 74, which may or may not be equipped with a coder, located outside the first case 10. The control connections of the jack 71 and a jack 75 for opening the gripper 68 are made by wires (not shown), which extend over the entire length of the jacket 72 and lead to external control means. The jacks 71 and 75 could be replaced by spring-loaded, static mechanical components, whose movements would be controlled by external motors and by cable transmissions stretched through the jacket 72.

The rotary arm 67 must also be vertically mobile in order to correctly position the container 4 for decontamination. For this purpose the spindle 73 slides vertically. The motor 74, on which the spindle 73 is dependent, is fixed to a platform 76, which slides on vertical standards 77 connected to a flange 78 for connecting to the jacket 72. The body of a jack 79 is fixed to the platform 76 and the end of the rod 80 is fixed to the flange 78. The jacks 79 operation on rod 80 therefore translates the desired movement to the platform 76.

Figure 7:
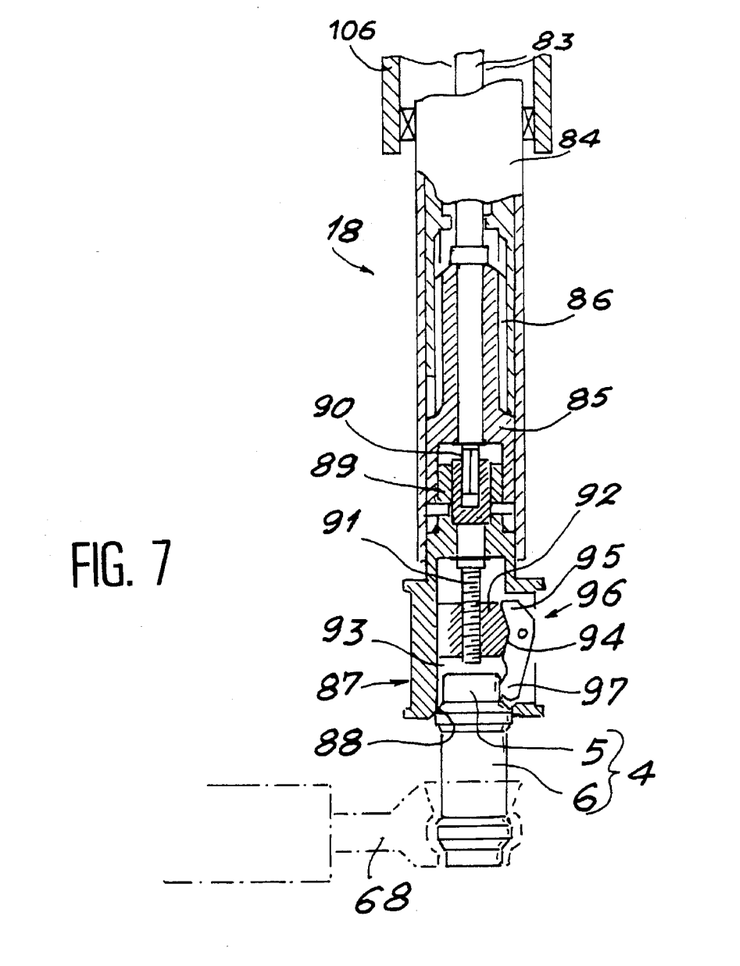
FIG. 7 Partial view of an unscrewing device in its most sophisticated version.
Figure 8:
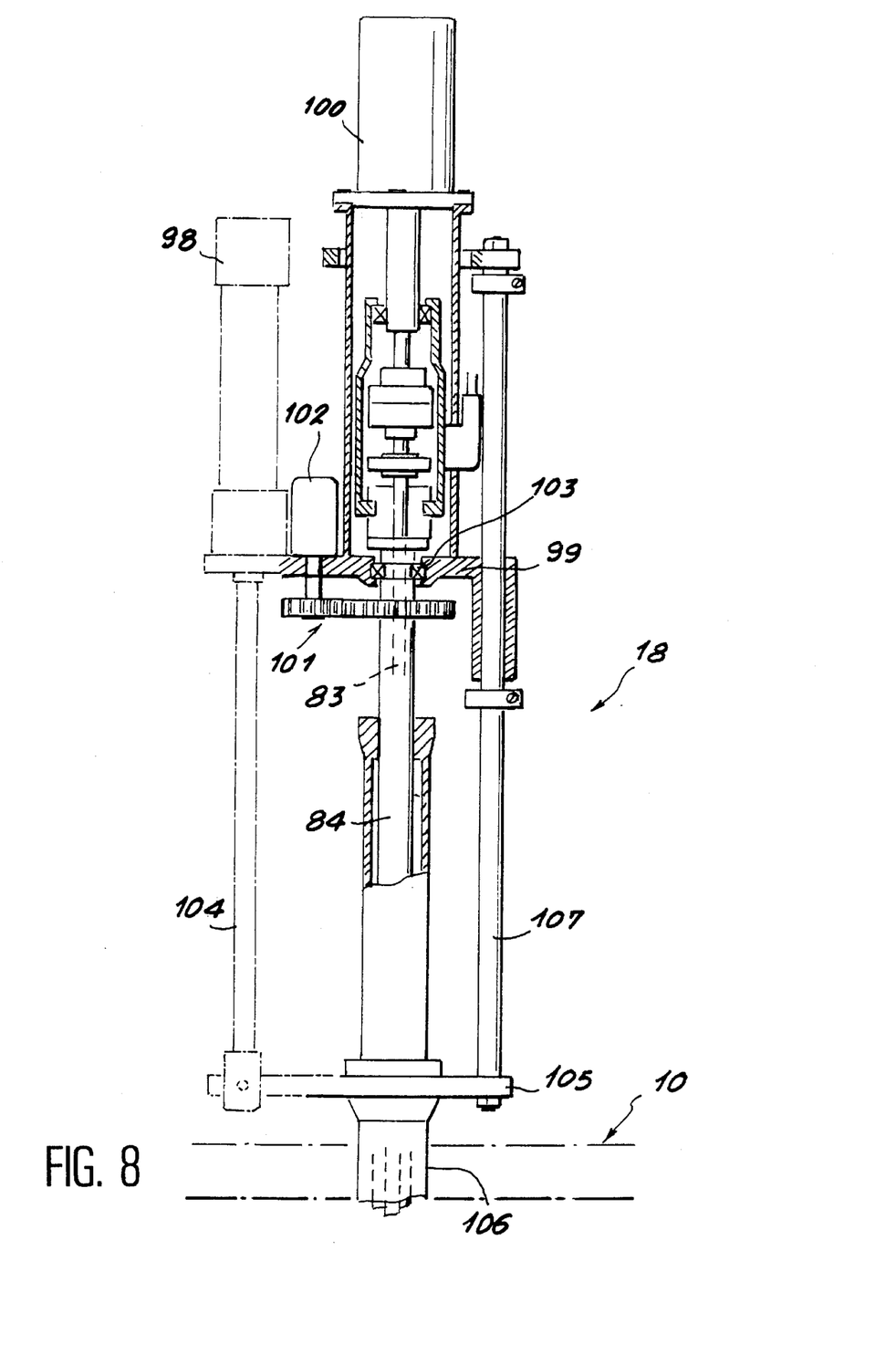
FIG. 8 Partial view of an unscrewing device in its most sophisticated version.

The unscrewing device 18, illustrated in FIGS. 7 and 8, has a spindle 83, which controls the unscrewing operation by vertically sliding in a jacket 84 under the action of a jack system identical to that of the turntable 16. The spindle 83 carries at its end a fitting 85 held to the spindle 83 by means of keys 86, which are fitted in corresponding grooves located on the interior of the end of the jacket 84. The fitting 85 is downwardly extended by a cap 87, which is substantially tubular, but whose bore is terminated by an internal, conical bearing surface 88. The bearing surface 88 flares towards the bottom and serves to frictionally receive the plug or stopper 5 of the container 4 in an interference-type fit, which is obtained by a downward movement of the spindle 83 and the fitting 85. To hold the container 4 in place when the bearing surface 88 engages the stopper 5, the jug 6 of the container 4 bears on the bottom 66, while being retained by the gripper 68. By adding a rotary movement to the sliding movement of the spindle 83, the fitting 85 rotates freely on the spindle 83. The fitting 85 no longer moves vertically and continues to firmly retain the stopper 5 by the cap 87. A bushing bush 89 retained in a cylindrical recess of the fitting 85 is turned by means of a square section end 90 of the spindle 83, which penetrates an opening of the same cross-sectional shape as the bushing 89. The bushing 89 is terminated by a screw 91. A nut 92 is engaged around the screw 91 and within the bore of the cap 87, which is terminated by an internal, conical bearing surface 88. The nut 92 has three wedge-shaped edges 94 uniformly distributed about the spindle 83, only one wedge-shaped edge 94 is shown. The nut 92 is thicker at mid-height at the location of the wedge-shaped edges 94. The bore of the cap 87 and the nut 92 do not have a circular internal cross-section, so that the nut 92 is stationary in rotation and moves vertically in accordance with the rotations of the screw 91 and the spindle 83. When the nut 92 rises the wedge-shaped edges 94 push the control arms 95 of the latches 96 which are in the form of bent levers. The other arms 97 of the control arms 95 bear on the stopper 5 in order to grip and retain the stopper 5. The stopper 5 is then unscrewed by rotating the jacket 84.

Referring to FIG. 8, there is a jack 98 which vertically displaces a base 99 in order to control the sliding movements of the jacket 84. Thus, the base 99 carries a roller bearing 103 on whose internal ring is suspended the jacket 84. The rotation of the jacket responsible for the unscrewing of the plug 5, is accomplished by means of a gear 101 connecting the intermediate jacket 84 to another motor 102 fixed to the base 99, which also carries a motor 100 for rotating the spindle 83. The rod 104 of the jack 98 is joined to a platform 105 integral with an external jacket 106 surrounding part of the length of the jacket 84 and which traverses the wall of the first case 10. The external jacket 106 is stationary and the platform 105 carries guide standards 107 about which slides the base 99. When the stopper 5 is unscrewed, the unscrewing device 18 is raised by a movement of the jack 98, thus carrying away the stopper 5 which is still held in the cap 87 and freeing the jug 6. The gripping arm 17 is then moved in order to align the jug 6 in front of the washers 20, 21, who's operation will be described in more detail below.

Figure 9:
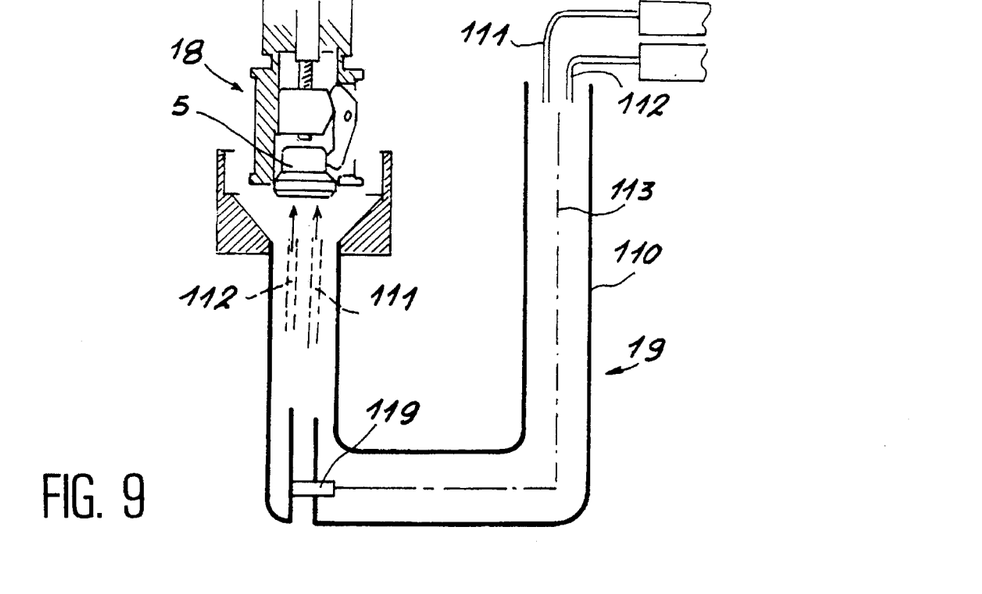
FIG. 9 A complete view of a container stopper washing apparatus.
Figure 10:
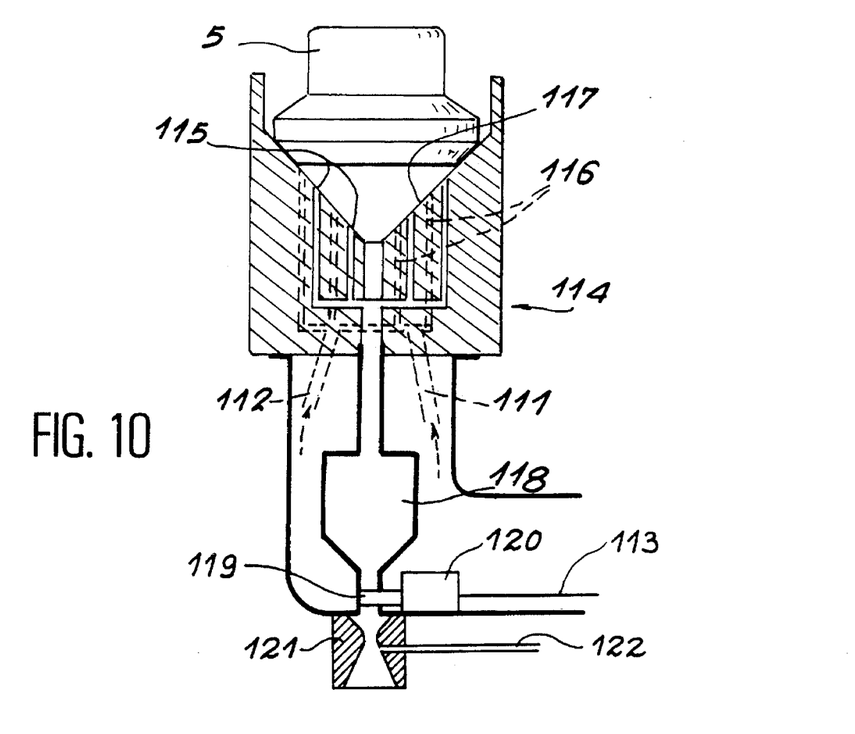
FIG. 10 A fragmentary view of a container stopper washing apparatus.

Referring to FIGS. 9 and 10, the stopper washer 19 is located at the end of a rotary arm 110 to position the stopper washer beneath the unscrewing device 18. The envelope of the rotary arm 110 houses water spraying pipes 111, air blowing pipes 112 and an electric wire or pneumatic control tube 113, The cup 114 is located at the free end of the rotary arm 110. The stopper 5, which is perfectly fitted to the cup 114, is introduced into the cup 114 by lowering the unscrewing device 18. The lowering of the unscrewing device 18 releases the latches 96 grip on the stopper. The water spraying pipe 111 is branched in the cup 114 so as to deliver water to the water spraying nozzles 115 located in the inner surface 117 and oriented so as to completely rinse the inner face of the plug 5. In the same way the air blowing pipe 112 is branched in the cup 114 so as to deliver air to the air blowing nozzles 116 located in the inner surface 117. The air dries the plug 5 after rinsing. The rinsing water containing contaminated products flows along the inner surface 117 of the cup 114 and leads to a tank 118 in the rotary arm 110. The inner surface 117 is funnel-shaped in order to permit said flow. The bottom of the tank 118 has a plug 119 controlled by an electrovalve or pneumovalve 120, which is controlled via the wire 113. When the tank 118 is full, it is brought above the effluent collector 27 by a rotation of the rotary arm 110 and the plug 119 is opened in order to empty it.

Alternatively, it is possible to use an air ejector 121, supplied with air by a tube 122, below the tank 118. The air ejection 121 takes place after bringing the cup 114 and it outlet orifice above the effluent collector 27. Its aim is to prevent an overpressure occurring beneath the stopper 5 during drying and to ensure that the contaminated droplets do not rise into the cup 114 by clearing the strap by which the stopper 5 bears on it. Instead of this the droplets are sucked up and all drop into the tank 118. If the air ejector 121 is combined with the strap 119, it makes it possible to carry out a final rinsing by which the cup 114 is entirely filled and then emptied. Air ejection during emptying makes it possible to completely remove the liquid. In this embodiment, decontamination is even more complete.

The stopper interior washer 29 is programmed, as are the two other washers 20 and 21, so as to only use a little washing liquid. Therefore the contaminated liquid volume is reduced. This advantage results from the total control of the process, the absence of wasted water by superfluous spraying and the elimination of passive decontamination in vessels where the stoppers 5 and the jugs 6 must be completely immersed.

Figures 11, 12, 13:
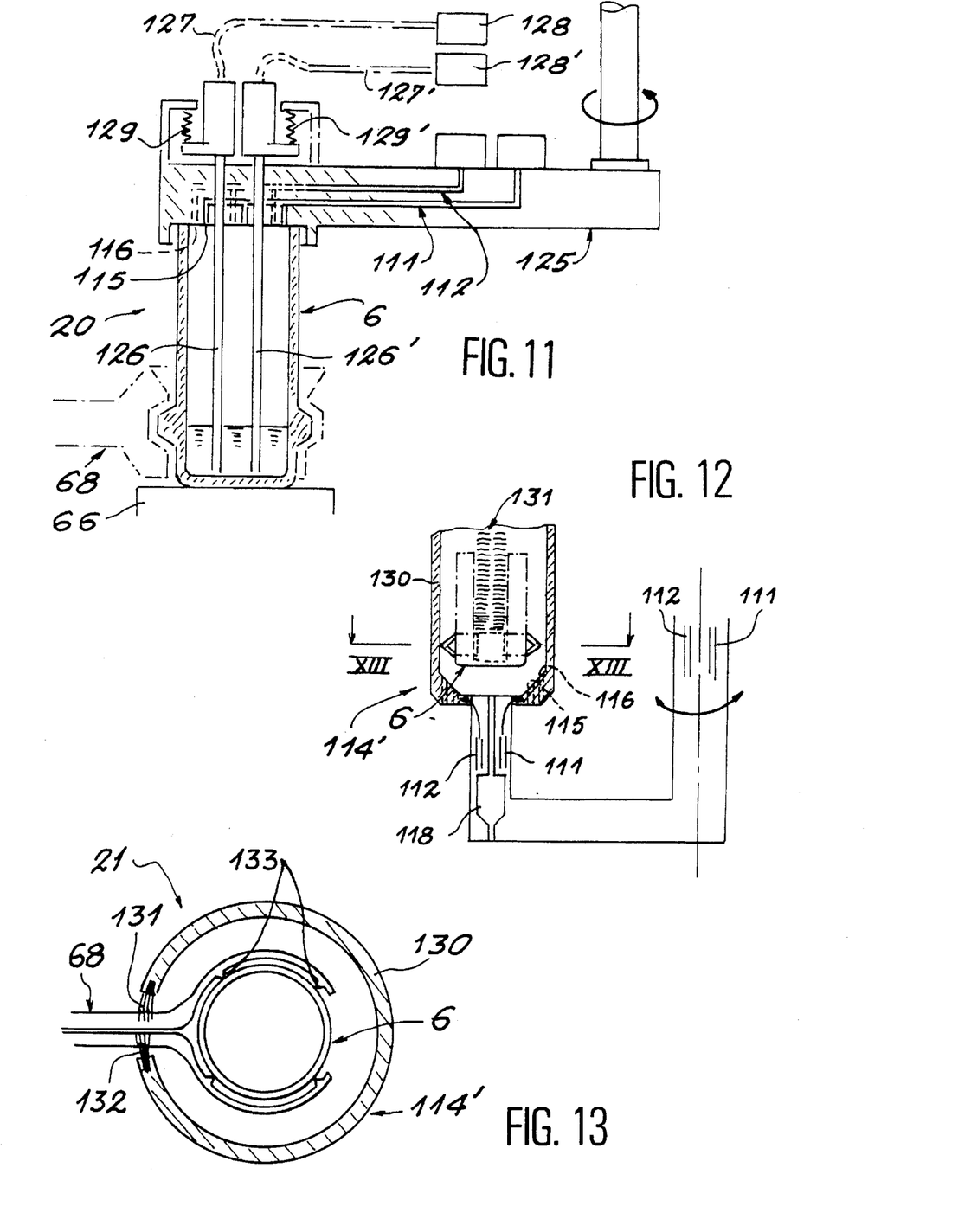
FIG. 11 A view of an apparatus for emptying and washing the interior of the containers.
FIG. 12 A complete view of an apparatus for washing the exterior of the containers.
FIG. 13 A sectional view along line XIII—XIII of FIG. 12 of an apparatus for washing the exterior of the container.

FIG. 11 shows the jug interior washer 20. The jug 6, still placed on the removable bottom 66, is held by the gripper 68 and placed below a rotary arm 125 of said washer 20. The jug 6 is raised until it is beneath the rotary arm 125. Water projecting nozzles 115 and air blowing nozzles 116, connected to supply pipes 111, 112 as described in association with the stopper washer 19, then spray into the jug 6. The rotary arm 125 also carries two syringe needles 126, 126' connected by flexible tubes 127, 127' to pumps 128, 128' located outside the first case 10. At least one of the needles 126, 126' penetrates to the bottom of the jug 6. The needles 126, 126' suspend from the rotary arm 125 by means of springs 129, 129'. The springs 129, 129' enable the needles 126, 126' to rise as soon as their end touches the bottom of the jug 6.

One of the needles 126 is used for sucking up the remainder of the contaminated sample filing the jug 6. The pump 128 is put into operation for producing this suction action. A small amount of prerinsing water is sprayed by the water projecting or spraying nozzles 115 onto the wall of the jug 6 in order to wash from it the contaminating particles covering it and any droplets which may remain. A further suction operation by the pump 128 makes it possible to absorb this relatively polluted liquid by the same needle 126. Rinsing with a larger quantity of water then takes place in order to completely wash the interior of the jug 6 and this liquid is sucked up in turn. Since this water is relatively unpolluted, the other needle 126' and the other pump 128' are used for this purpose.

The pumps 128, 128' can be the same pumps as used elsewhere in the installation for performing liquid samplings. Here again an air ejector or an equivalent suction means can be added in order to avoid the creation of an overpressure that may create contaminated liquid leaks, during rinsing and drying.

The jug 6 is then dried with air blown from blowing nozzles 116. The jug 6 is then lowered and removed and the needles 126, 126' are positioned above the recycling collector 26 and the effluent collector 27. The content of the first needle 126 is ejected into the recycling collector 26 and the contents of the second needle 126' is ejected into the effluent collector 27. Thus, the recycling collector 26 collects highly contaminated liquid and is passed to a reprocessing installation, which is specifically isolated from the exterior in which working takes place on contaminated liquids and from which pass the filled containers 4, which is easy to carry out in a relatively inexpensive manner because the volume of the liquid is small. There is no need to take the same precautions with the tank 28, which collects the relatively unpolluted effluents and which can therefore be designed and transported on lesser standards.

Referring to FIGS. 12 and 13, the jug 6 is then brought to the jug exterior washer 21. Similar to the plug washer 19, the jug exterior washer 21 has rinsing and blowing pipes 111, 112, corresponding nozzles 115, 116, as well as a cup 114' into which the nozzles 115, 116 issue in the same way. Compared with the cup 114, the cup 114' has an edge 130 which is significantly higher, so that the jug 6 can be introduced into it and which has a vertical slot 131 occupied by a leaf joint 132 in order to enable the gripper 68 to be lowered through the cup 114'.

The gripper 68 is equipped with points 133 on the inner face of its jaws in such a way that the decontamination water cleans both the entire exterior of the jug 6 and the gripper 68 and consequently no uncleaned surface is created between the gripper 68 and the jug 6. The washing action simultaneously washes the object to be cleaned, the interior of the volume and the gripping tool, so as to prevent the accumulation or deposition of contaminated droplets.

The exterior of the jug 6 is rinsed and dried in order to remove contaminating particles which will have collected there during its passage through the pneumatic transfer system or the like. The contaminated rinsing liquid falls into a tank 118. As described in reference to the stopper washer 19, the tank 118 is opened above the effluent collector 27. Reference should again be made to FIG. 1 for the remainder of the description. Stopper 5 and the jug 6 are dropped into their respective discharge systems 22, 23, so that another container 4 waiting on the turntable 16 may be decontaminated. The discharge systems 22, 23 have vertical entrance hoppers respectively 142, 142', where the stopper vertical entrance hopper 142 is located immediately below the unscrewing device 18 and the jug vertical entrance hopper 142' is located beneath a position accessible to the gripping arm 17. To drop the stopper 5 into the stopper vertical entrance hopper 142, the latches 96 must be retracted. To drop the jug 6 into the jug vertical entrance hopper 142', the gripping arm 17 must be positioned over the hopper 142', the bottom 66 must be retracted and the gripper 68 opened. On reaching the bottom of the hoppers 142, 142', the stopper 5 and the jug 6 respectively start the rise of hinged pipes 143, 143' respectively by means of compressed air bursts produced by sources 144, 144'. The pipes could also be raised using sucking air by an apparatus placed downwstream of the hinged pipes 143, 143'. The plug 5 and the jug 6 pass in front of the radioactivity counter 24.

Figure 14:
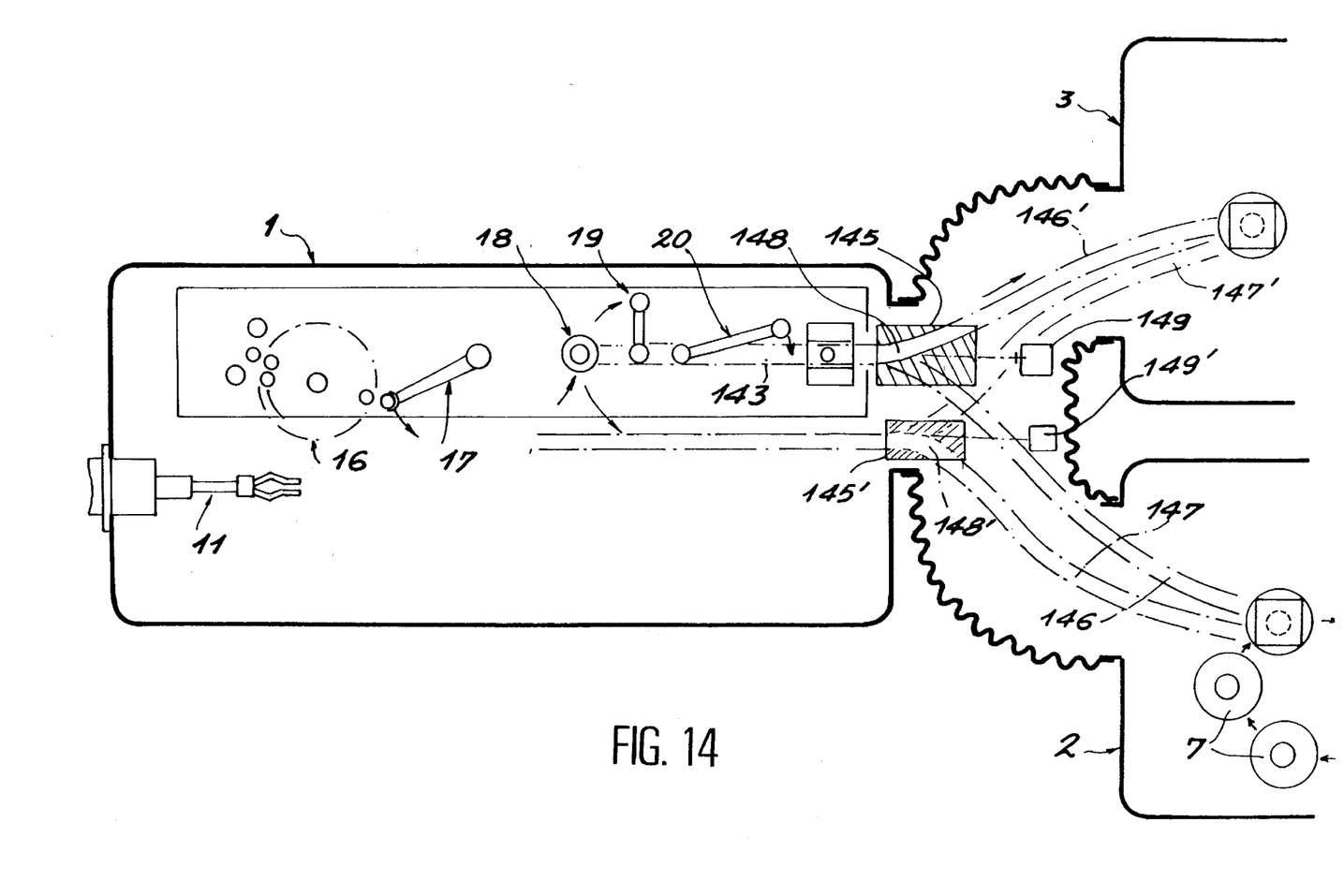
FIG. 14 A plan view of a preferred embodiment of the decontamination unit.

Referring to FIGS. 1 and 14, the hinged pipes 143, 143' branch on reaching a forking drum 145 or 145' into two pipes 146 or 146' and 147 or 147'. The stoppers 5 are supplied to pipes 146, 146'. The jugs 6 are supplied to pipes 147, 147'. The drums 145, 145' have an inwardly curved recess 148 or 148' as an extension of the entrance pipe 143 or 143', which is located in the entrance pipes' 143, 143' axis. The other end of the drums 145, 145' extend to the pipes 146 and 146' or 147 and 147'. The drums 145, 145' are rotated by a motor 149 or 149'. The plugs 5 and the jugs 6 thus reach either the first scrapping enclosure 2 or the second scrapping enclosure 3, where one scrapping enclosure is allocated to slightly contaminated containers 4, and the other to the more contaminated containers 4, whose storage constraints are more strict. The scrapping enclosure allocated to move contaminated containers is optionally more strongly shielded than the other, but otherwise the enclosures' construction is substantially identical. Thus, a description will only be given of the enclosure 2, into which issue the pipes 146, 147 and for this purpose reference should be made to FIGS. 1 and 15. The first of these pipe 146 issues directly above a waste canister 7. Canister 7 is part of a series of waste canisters placed on a closed loop, oblong conveying track 150, which is defined at its internal and external perimeters by two borders 151, 152. In addition, there are two rollers 153, 153' at the two ends of the central space enclosed by the track 150 and a belt 154 is stretched between the two rollers 153, 153'. The belt 154 carries dogs 155 for advancing the waste canisters 7. One of the rollers 153 is rotated by the action of a drive motor 156, in turn rotating the belt 154. Thus, each of the waste canisters 7 passes in turn below the outlet orifice of the pipe 146 and a discharge hopper 157, which is itself positioned above two pairs of crushing rollers 158, 159.

Figure 15:
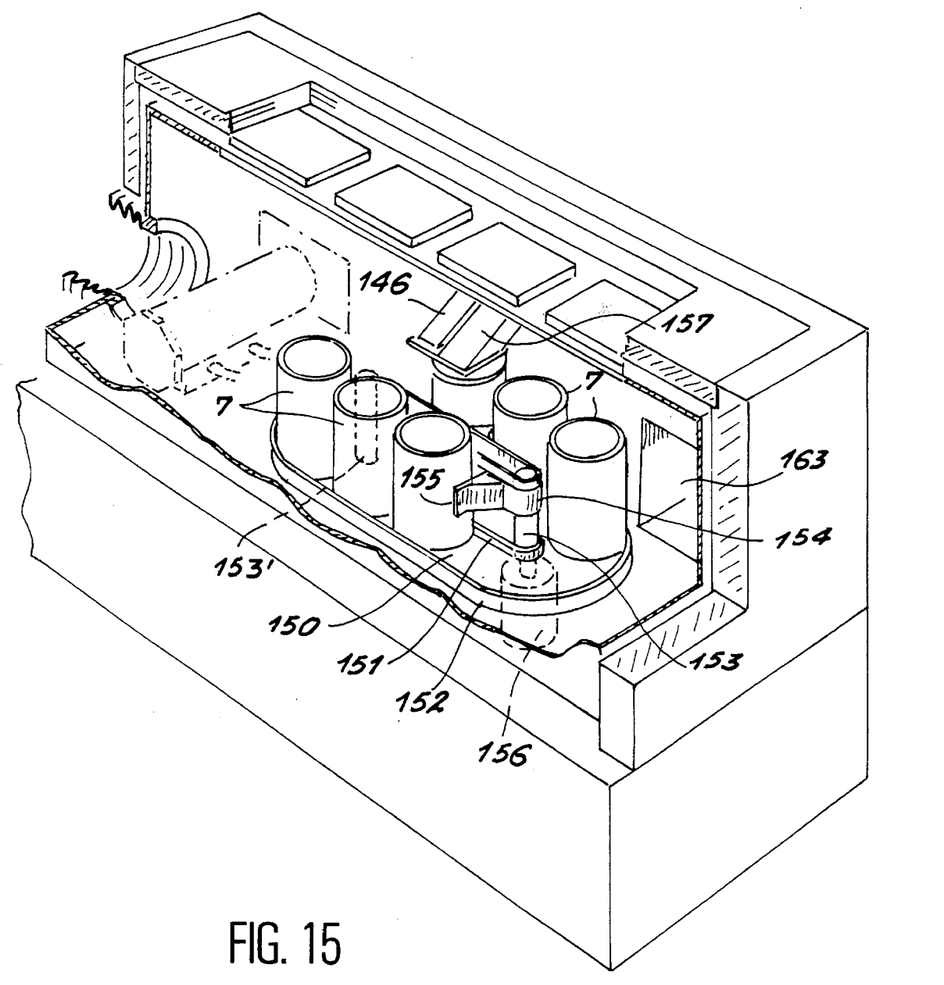
FIG. 15 A perspective view of the container scrapping means.

The pipe 147 for conveying the jugs 6 of containers 4 passes, above the crushing rollers 158, 159, into an introduction hopper 160. The jugs 6 are discharged from pipe 147 then slide into the crushing rollers 158, 159, where they are crushed into small fragments. Crushing the jugs reduces their volume in the canisters 7. It is recommended either to shred the plastic jugs 6 by means of knife-covered rollers, or better still to embrittle them cryogenically using carbon dioxide gas or liquid nitrogen from commercial cylinders 161. The freezing substance is automatically released in small quantities through opening 162 whenever a jug 6 passes into the hopper 160. This cools the jugs 6 below their embrittlement temperature and the jug 6 is shattered between the substantially smooth rollers 158, 159, so that the volume is greatly reduced. When the waste canister 7 is full another is rotated into its place and the full canisters 7 arrive in front of a lock 163, which is then opened in order to remove the canister 7 and replace it with another canister, which will subsequently arrive beneath the orifice of the pipe 146 and beneath the discharge hopper 157 after having traversed the other side of the track 150.

The hinged pipes 143, 143' rise up to the enclosures 2 and 3 in order to wash them, more particularly when contaminated particles have been deposited thereon, because they can move towards the enclosures 2 and 3, which communicate with the exterior and disturb the measurements of the radioactivity sensor 24. Thus, it is possible to have sprinkling circuits 164, 164', which issue into the hinged pipes 143, 143' downstream of the radioactivity counter 24, e.g. level with the bellows 12. The sprinkling water flows towards the first shielded enclosure 1 and leaves the hinged pipes 143, 143' by a draining orifice 165 or 165' after rinsing the same. The water then flows into the effluent collector 27. For this purpose it is useful for the bottom of the first case 10 to be funnel-shaped. The vapours, fumes and aerosols accumulated in case 10 may be allowed to condense they may be removed by a not shown ventilation circuit. Gaskets are provided at all the orifices of the first case 10 in order to make them sealed.

Finally, a crushing installation can be provided for the plugs or stoppers, but the possible volume gain from such an arrangement is not very large. It would also be possible to do without the crushing installation in the scrapping enclosure allocated to more contaminated jugs 6, because their number is smaller and they consequently only occupy a limited volume.

I claim:

1. Unit for the decontamination of containers containing radioactive liquid and having a jug portion and a sealing stopper portion, said unit comprising means for opening, emptying, washing and drying the containers, said means for opening, emptying, washing and drying arranged in chain form, an outlet for the containers downstream of said opening, emptying, washing and drying means and connected to scrapping means, a residual radiation contamination counter at said outlet, said outlet having a branch downstream of said counter, and means for receiving and regulating the flow of containers located upstream of the container opening means.

2. Unit according to claim 1, wherein said outlet has a rising pipe preceding the counter.

3. Unit according to claim 1, wherein said outlet has crushing means preceding the scrapping means.

4. Unit according to claim 3 wherein said crushing means overhangs said scrapping means and said scrapping means comprises waste canisters.

5. Unit according to claim 4, wherein said outlet has means for cooling the containers to a fragile state prior to said crushing means.

6. Unit according to claim 5, wherein said cooling means includes a gas blowing member for injecting gas from a cylinder.

7. Unit according to claim 1, wherein said receiving and regulating means is a turntable having a plurality of individual reception cavities for the containers.

8. Unit according to claim 1, further comprising means for transferring containers from said receiving and regulating means through said means for opening, emptying, washing and drying the containers, and to said outlet.

9. Unit according to claim 8, wherein said transfer means is a rotating arm having a container reception end.

10. Unit according to claim 1, wherein said washing means includes means for washing the interior of the jug portion of the container, means for washing the exterior of the jug portion of the container, and means for washing the interior of the sealing stopper portion of the container.

11. Unit according to claim 1, wherein said container emptying means are integral with the container washing means.

12. Unit according to claim 1, wherein said container emptying means includes preliminary emptying means associated with a highly contaminated liquid recycling collector and final emptying means employed after washing and associated with a relatively uncontaminated effluent collector.

13. Unit according to claim 1, wherein said drying means comprises gas blowing circuits integral with said washing means.

14. Unit according to claim 1, wherein said opening means includes means for receiving the sealing stopper portion of the container and said opening means overhangs an outlet for the stopper portions.

* * * * *